(12) United States Patent
Menkes et al.

(10) Patent No.: US 6,175,753 B1
(45) Date of Patent: Jan. 16, 2001

(54) METHODS AND MECHANISMS FOR QUICK-PLACEMENT ELECTROENCEPHALOGRAM (EEG) ELECTRODES

(75) Inventors: Alex Menkes; John R. Sakers, both of Baltimore; Eva Jane Dixon, Columbia; F. Scott Corey, Severna Park, all of MD (US)

(73) Assignee: Baltimore Biomedical, Inc., Baltimore, MD (US)

( * ) Notice: Under 35 U.S.C. 154(b), the term of this patent shall be extended for 0 days.

(21) Appl. No.: 09/346,693

(22) Filed: Jul. 2, 1999

Related U.S. Application Data

(60) Provisional application No. 60/091,681, filed on Jul. 2, 1998.

(51) Int. Cl.[7] .................................................. A61B 5/0478
(52) U.S. Cl. .......................................... 600/386; 600/383
(58) Field of Search ................................. 600/382, 383, 600/386; 607/115, 149, 139, 79

(56) References Cited

U.S. PATENT DOCUMENTS

| | | | |
|---|---|---|---|
| 3,469,577 | * | 9/1969 | Kater ..................................... 600/386 |
| 3,896,790 | * | 7/1975 | Dikman ................................. 600/386 |
| 4,067,321 | * | 1/1978 | Oda et al. ............................. 600/386 |
| 4,632,120 | * | 12/1986 | Sherwin et al. ...................... 600/386 |
| 4,709,702 | * | 12/1987 | Sherwin ................................ 600/386 |
| 4,936,306 | * | 6/1990 | Doty ..................................... 600/386 |
| 5,222,498 | * | 6/1993 | Neward ................................ 600/386 |

FOREIGN PATENT DOCUMENTS

405026909 * 10/1993 (JP) .............................. A61B/5/0408

* cited by examiner

*Primary Examiner*—Jeffrey R. Jastrzab
(74) *Attorney, Agent, or Firm*—Dorsey & Whitney LLP

(57) ABSTRACT

This invention provides a quick-placement EEG electrode. The EEG electrode is fixed to a patient's scalp by a first element working in conjunction with a second element to trap hair and hold the EEG electrode in place. The EEG electrode contains a sponge that when compressed, dispenses electrolytic gel, acts as a shock absorber, and maintains contact with the scalp. The EEG electrode has a quick release mechanism for easy removal of the EEG electrode from the patient's scalp.

3 Claims, 11 Drawing Sheets

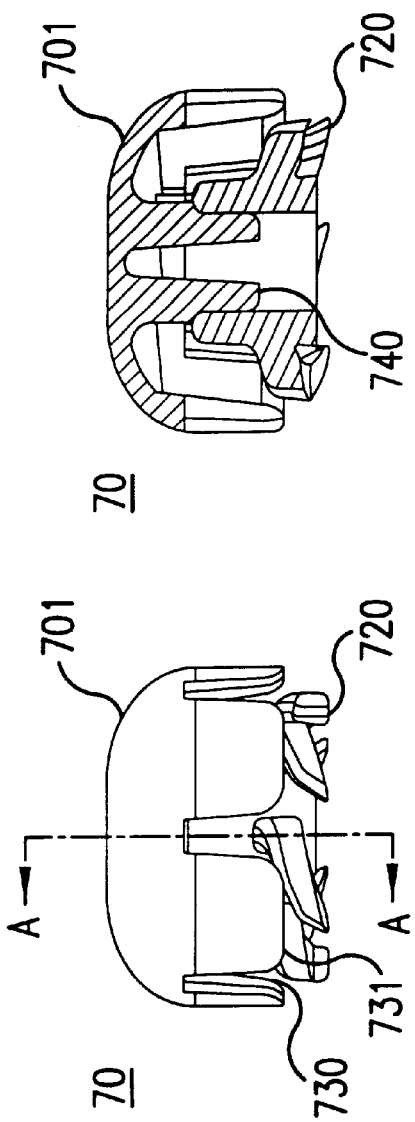
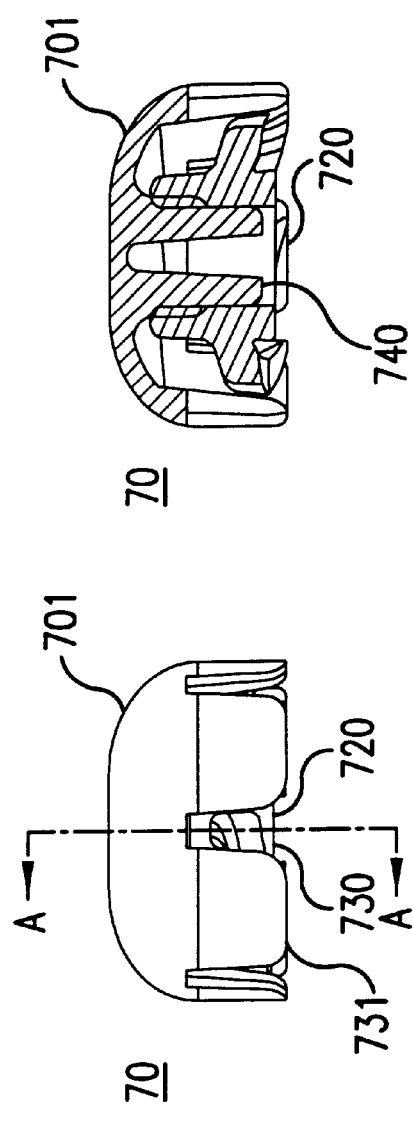
FIG.10A
FIG.10B
FIG.10C
FIG.10D

METHODS AND MECHANISMS FOR QUICK-PLACEMENT ELECTROENCEPHALOGRAM (EEG) ELECTRODES

This non-provisional application claims the benefit of provisional application Serial No. 60/091681, filed Jul. 2, 1998. The provisional application is incorporated herein by reference.

STATEMENT REGARDING FEDERALLY SPONSORED RESEARCH OR DEVELOPMENT

This invention was made with government support under grant number 1R43MH59444 awarded by National Institute of Health. The government has certain rights in the invention.

TECHNICAL FIELD

This invention relates to electroencephalogram (EEG) electrodes. More particularly, the invention relates to EEG electrodes that can be quickly applied and removed from a patient's scalp. The invention also relates to methods for quickly and easily applying and removing the EEG electrodes from the patient's scalp.

BACKGROUND ART

Attachment devices exist for fixing EEG electrodes to a patient's scalp. These devices may use colloidal glue, adhesive tape or bandages. EEG electrodes may also be attached by incorporating them into web matrix helmets. Placing and removing these EEG electrodes from a patient's scalp is time consuming. The EEG electrodes are uncomfortable to wear and may loose signal contact during extended ambulatory monitoring.

Web matrix helmets are headpieces made of a webbing material. Web matrix helmets are fastened to the patient'head by means of a chin strap and/or a neck strap with scalp-pattern electrodes attached along the undersurface of the web material. Web matrix helmets cannot be used unobtrusively in ambulatory settings. Furthermore, each contact area on the patient's head must be thickly coated with an electrolytic gel to obtain good signal quality. Even with this preparation, since the electrodes themselves trap large quantities of hair between the electrode body and the scalp, there is a possibility for signal loss from any one electrode. Also, during the course of long-term monitoring, re-application of electrolytic gel is often necessary to maintain signal quality. Lastly, web matrix helmets do not fit all head shapes and sizes, making electrode placements problematic with some patients.

Scalp placement electrodes may also be attached to the patient by means of an adhesive paste. The electrode is pressed into a large amount of electrolytic adhesive paste or gel applied at the desired placement site, and then the electrode is taped in place to allow the adhesive to set. The electrodes are obtrusive, and a large amount of electrolytic gel is needed to maintain proper contact because the electrode-scalp interface tends to dry out through evaporation. In addition, adhesive-attached scalp electrodes cannot be used in most ambulatory settings because they tend to become dislodged during normal movement or activity. Finally, this type of placement entails a messy and time consuming clean-up.

Colloidal glues achieve stronger bonding between the electrode and the scalp, but their use is both time and labor intensive. In a typical application, electrolytic gel is applied to the patient's scalp, the electrode is seated and taped in place, and the colloidal glue is applied and allowed to dry. This process can take 7–15 minutes per electrode. Removing the electrode requires applying a solvent, and the patient is inconvenienced because the collodion remains in the hair. In addition, the collodion and solvents emit strong fumes, limiting their use to specially ventilated rooms. Also, because the collodion can bond to unintended surfaces, special care must be used not to touch any other material while gluing the electrodes in place. Lastly, many patients may experience scalp irritation due to sensitivity or allergic reactions to the collodion.

SUMMARY OF THE INVENTION

This invention is directed to a quick-placement electroencephalogram (EEG) electrode that may be used for monitoring brain wave activity, for example. The quick-placement EEG electrode includes a first element and a second element. The second element may be constructed of two pieces, such as a plunger and a grabbing element, for example. When the quick-placement EEG electrode is assembled, the first element is connected to the second element. Alternately, the first and second element may be molded as a single piece capable of functioning as an EEG electrode.

The quick-placement EEG electrode is designed to clamp to a patient'share by trapping hair between the first element and the second element, or in the grabbing element alone. A sponge carried in the second element and containing electrolytic gel may be compressed by the mating of the first element to the second element, causing release of the gel at the scalp contact point. The compressed sponge counters a downward force exerted on the trapped hair by the grabbing element, acts as a shock absorber, and maintains constant contact between the scalp and the electrode. Finally, the quick-placement EEG electrode is easily removed by releasing the first and second elements. The quick-placement EEG electrode maximizes the accuracy of EEG readings and exploits specific characteristics of electrolytic gel-type electrodes for long term monitoring. Dissipation of the gel from movement (friction) is minimized because the EEG electrode is held securely in place by gripping the patient's hair. In addition, the design provides a covering for the sponge saturated with electrolytic gel. This covering traps the electrolytic gel between the electrode and the scalp, thus minimizing evaporation and allowing the gel to remain stable over a longer time. Because it is attached to the hair, the quick-placement EEG electrode may be quickly applied and removed. Moreover, low visibility of the EEG electrode makes it more practical for long-term ambulatory monitoring.

BRIEF DESCRIPTION OF THE DRAWINGS

The invention is described with reference to the following drawings wherein like numerals refer to like elements, and wherein:

FIGS. 10a–10d are side views and sectional views of a quick-placement EEG electrode;

DETAILED DESCRIPTION OF PREFERRED EMBODIMENTS

EEG electrodes are important devices for measuring the electrical activity that is always present in the brain and for acquiring EEG brainwave recordings. EEG recordings are useful for a broad range of applications including medical screening and diagnosis.

As a diagnostic aid, the rapid placement of EEG electrodes can be crucial in hospital and emergency room settings where medical or technical personnel use EEG recordings for diagnosing a variety of neurological disorders. In addition, the rapid and convenient placement of EEG electrodes for screening purposes in out-patient settings minimizes inconvenience to the patient.

Often, the most crucial EEG readings are obtained while unforeseen brain activity occurs. For example, EEG measurements taken during a seizure can help to determine the seizure focus region (i.e., the part of the brain in which the seizure activity begins). Other uses for EEG electrodes include measuring electrical brain activity during sleep. As such, an EEG electrode that is both comfortable and minimally disrupts the patient'sleep pattern is required for diagnosing sleep disorders. The availability of a rapid and conveniently deployed electrode is imperative for the development of portable consumer brain monitoring devices. A significant example would be an awareness device that monitors brain waves to prevent commercial drivers and others performing critical but repetitive operations from falling asleep.

Figure 1:
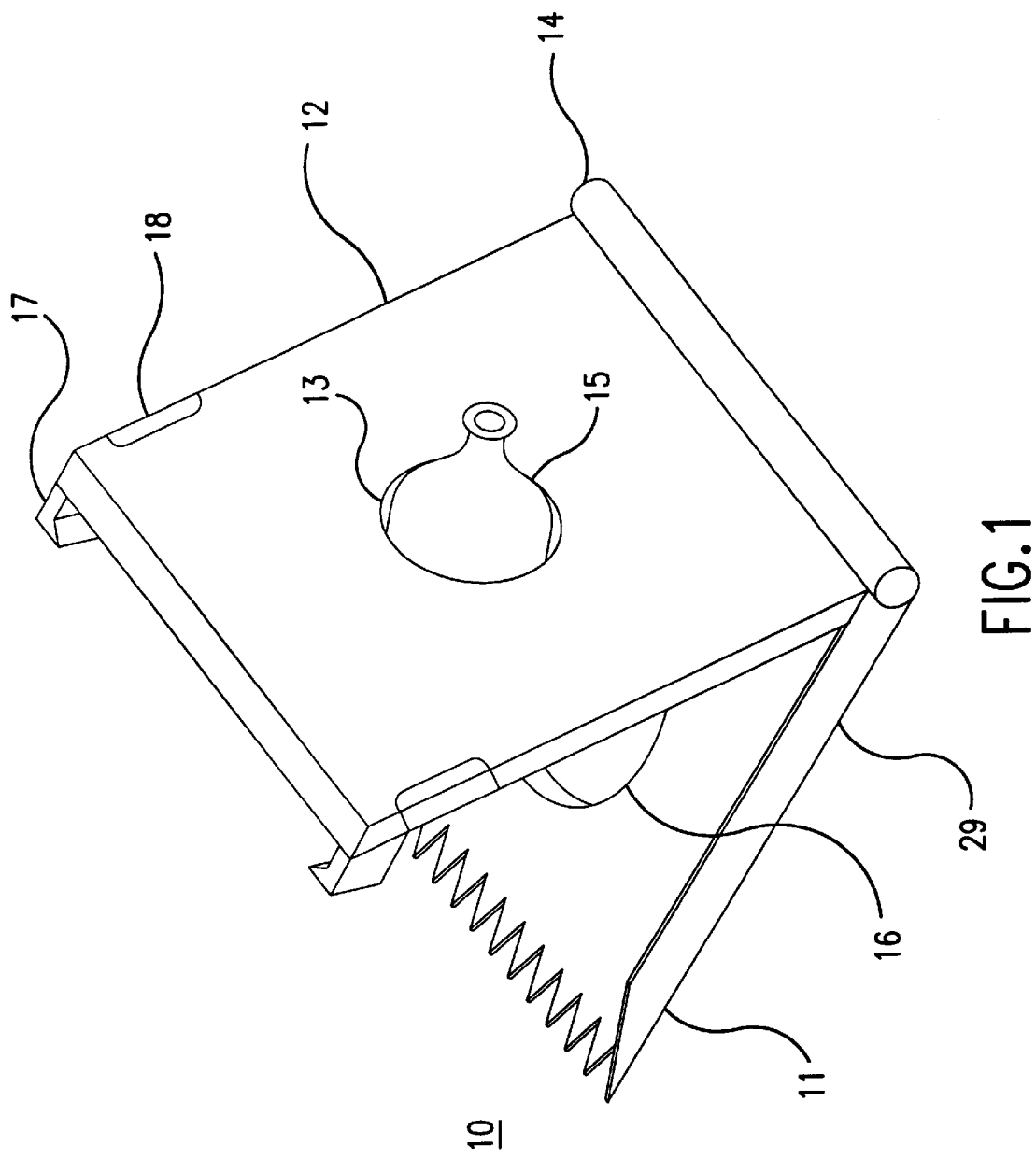
FIG. 1 is a perspective view of a quick-placement EEG electrode showing its general configuration.

FIG. 1 shows a quick-placement EEG electrode 10 for use in recording brain wave activity, for example. The EEG electrode includes a first element, and one or more second elements that connect to the first element and that operate in conjunction with the first element. In particular, the second element is movable relative to the first element. In FIG. 1, the first element is shown as a "Nif" comb 11 having serrated openings at one end, and the second element is a cap 12 and a plunger 13. The comb 11 is attached to the second element by a spring loaded hinge assembly 14. The comb 11 includes a circular opening 16 to accept a sponge (not shown in FIG. 1). A bottom portion 29 of the comb 11 may be flat or curved to allow the comb 11 to easily glide along the patient'sscalp. The bottom portion 29 may also be padded or coated to ease application and comfort for the patient. Other configurations for the first element are also possible, as will be described later. For example, the first element could be square or any rectangle. The plunger 13 penetrates the cap 11 through an opening 15. As shown in FIG. 1, the opening 15 is circular, however the opening may be any suitable shape, including that of any polygon. The comb 12 also includes two spring loaded locking tabs 17 that are released by pressing release tabs 18.

Figure 2:
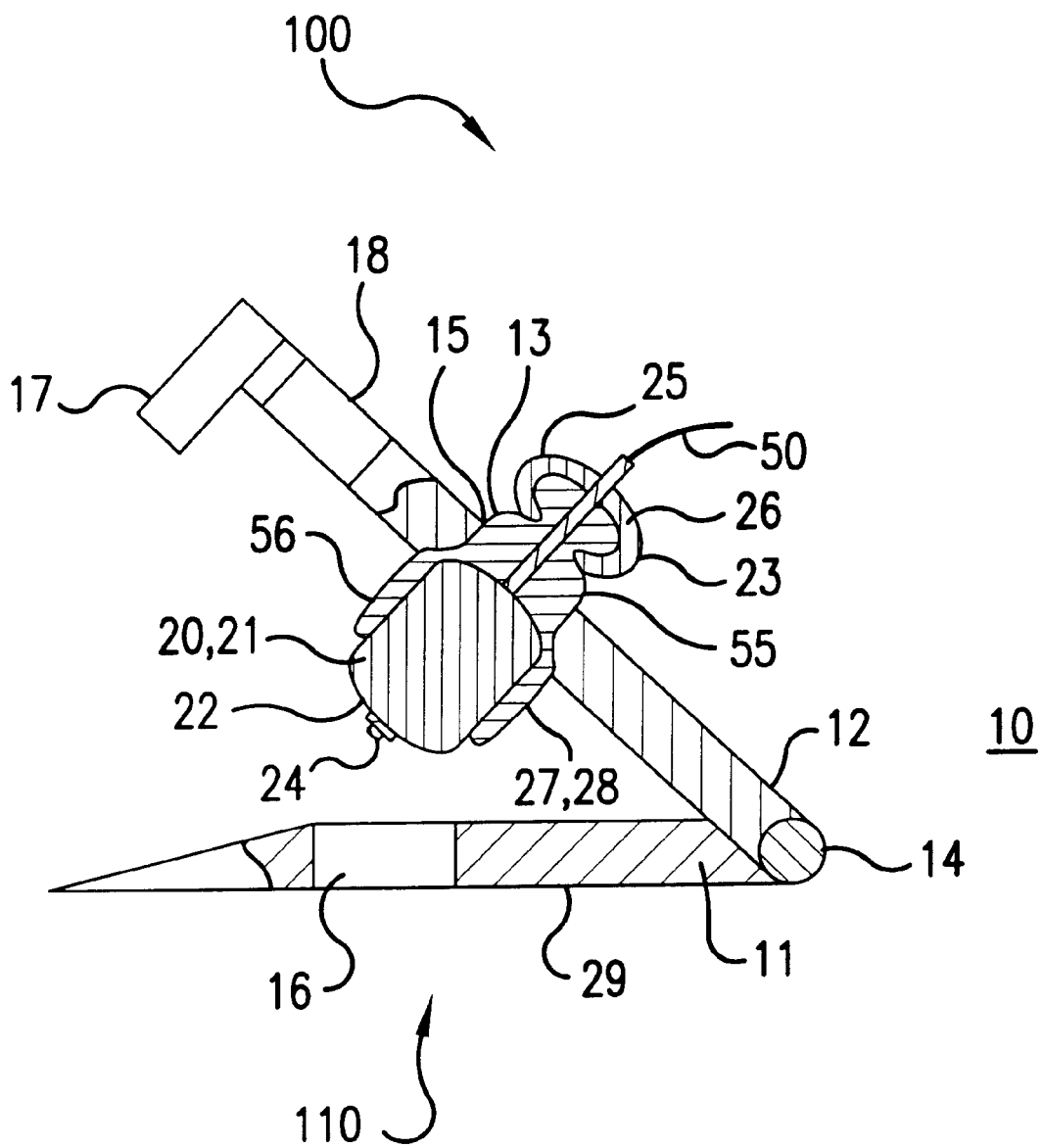
FIG. 2 is a cut-away view of the quick-placement EEG electrode of FIG. 1.

FIG. 2 is a side view of the EEG electrode 10 showing the comb 11, the cap 12, and the plunger 13 in the disengaged position. As shown in FIG. 2, the cap 12 includes a receptacle 23 that is used to attach the EEG electrode 10 to a recording device (not shown).

Referring to FIG. 2, the plunger 13 includes an upper section 55 and a lower section 56. In FIG. 2, the upper section 55 and the lower section 56 are shown as cylindrical. However, the upper section 55 and the lower section 56 can be in the shape of any polygon to match the corresponding shape of the opening. The upper section 55 projects through the opening 15. A diameter of the lower section 56 is larger than a diameter of the opening 15, thereby preventing the plunger 13 from exiting through the circular opening 15. The plunger 13 includes a sponge 20, saturated with an electrolytic gel 21, and at least partly enclosed by a cover or membrane 22, fixably attached to the underside of the plunger 13. The sponge 20 may have a cross-section that corresponds to that of the opening 15 in the comb 11. For example, the sponge 20 may be cylindrical or in the shape of any polygon. Using the sponge 20 saturated with the electrolytic gel 21 ensures that the electrolytic gel 21 will not evaporate during the time that the EEG electrode 10 is attached to the patient's scalp.

The sponge 20 may be attached to the EEG electrode 10 immediately prior to use, or may be attached when the EEG electrode 10 is manufactured, for example. Various methods may be used to attach the membrane 22, for example, by gluing or wrapping the membrane 22 around the sponge 20 and then attaching the membrane 22 to the underside of the cap 12. The membrane 22 may be attached to the underside of the cap 12 by gluing, for example. The membrane 22 may be any suitable material such as a man-made polymeric material. The membrane 22 prevents the electrolytic gel 21 from leaking from the sponge 20 or evaporating while the EEG electrode 10 is not in use. A bottom 24 of the sponge 20 defines an electrode contact point. The electrode contact point 24 is part of a path for transmitting brain waves or similar information to the EEG electrode 10.

The EEG electrode 10 is connected to an EEG lead wire 50 at a receptacle 23. Various known connection devices may be used for this purpose, such as a collar connector 25, which is placed over the plunger 13. The collar connector 25 is a "D" snap-in safety connector. Attached to the collar connector 25 is a leg wire 26. When pressed onto the top of the plunger 13, the collar connector 25 locks in place in the receptacle 23. The leg wire 26 on the collar connector 25 contacts a conductive layer, which will be described later, at the receptacle 23, completing an EEG circuit. This type of collar connector 25 and the leg wire 26 are commercially available and commonly used with other EEG electrodes. Other commercially available connectors and leg wires may also be used.

The EEG electrode 10 shown in FIG. 2 may be of a small size with the area of the cap 12 being about 2 cm square, for example. The cap 12 may be injection molded using acrylonitrile-butadiene-styrene (ABS) or similar material. The comb 11 may be injected molded using Elastollan® thermoplastic polyurethane (TPU) or similar material or comprised of spring steel. The plunger 13 may be injection molded and may be made of a material similar to that of the comb 11 or an electrically conductive material. The plunger 13 may be coated with a conducting material that provides a current path between the electrolytic gel 21 and the leg wire 26. As shown in FIG. 2, the plunger 13 may be coated with a silver (Ag) layer 27, for example. Through an additional electrolytic process, a silver chloride (AgCI) layer 28 may be applied to the silver layer 27. The resulting Ag—AgCI layer 27, 28 conducts current from the electrolytic gel 21 to the leg wire 26. Other known coating and conductive layers may also be used with the plunger 13.

Once the EEG lead wire 50 is connected to the EEG electrode 10, the EEG electrode 10 is placed against the hair at a point on the patient's scalp where recording is desired, with the bottom portion 29 of the comb contacting the scalp. The comb 11 is then slid along the scalp, and hairs enter the serrated openings of the comb 11. The cap 12 is then depressed to trap the scalp hairs and hold the EEG electrode in place. In operation, a downward force shown generally by the arrow 100 applied to the top of the cap 12 causes scalp hairs to be securely trapped between the cap 12 and the comb 11, and securely holds the EEG electrode 10 in place against the scalp to maximize contact of the EEG electrode 10 with the scalp. The EEG electrode 10 is designed such that the trapped hairs exert a downward force to hold the EEG electrode 10 against the scalp.

The same downward force 100 on the plunger 13 that traps the hairs between the cap 12 and the comb 11, also causes rapid compression of the sponge 20 in the center of the plunger 13. The compression of the sponge 20 ruptures the membrane 22, causing the electrolytic gel 21 to be applied to the scalp contact point. The membrane 22 is designed such that when it ruptures, the ruptured sections are pulled away from the scalp contact point, thereby ensuring good electrical connection between the scalp contact point and the sponge 20. For example, lower cylindrical sides of the membrane 22 are not glued to the sponge 20. When the sponge 20 is compressed, the lower cylindrical sides retract upward along sides of the sponge 20, withdrawing the ruptured sections from the scalp contact point.

In addition to supplying the electrolytic gel 21, the compressed sponge 20 provides an upward force, shown generally by arrow 110, opposing a downward force being exerted by the trapped hair, thereby creating an equilibrium system. The sponge 20, acting as a shock absorber, maintains constant contact with the scalp, even if the EEG electrode 10 moves up or down in relation to the scalp.

To lock the cap 12 into the comb 11, downward force is applied to the cap 12. The downward force on the cap 12 causes a slight deformation of the spring loaded locking tabs 17 on the cap 12. This deformation allows the locking tabs 17 to slide over an upper portion of the comb 11. The locking tabs 17 then capture the comb 1, and lock the cap 12 in a closed position. To remove the EEG electrode 10 from the patient's scalp, the release tabs 18 are pressed inward. This causes the locking tabs 17 to retract from the comb 11. The EEG electrode 10 may then be removed.

Figure 3:
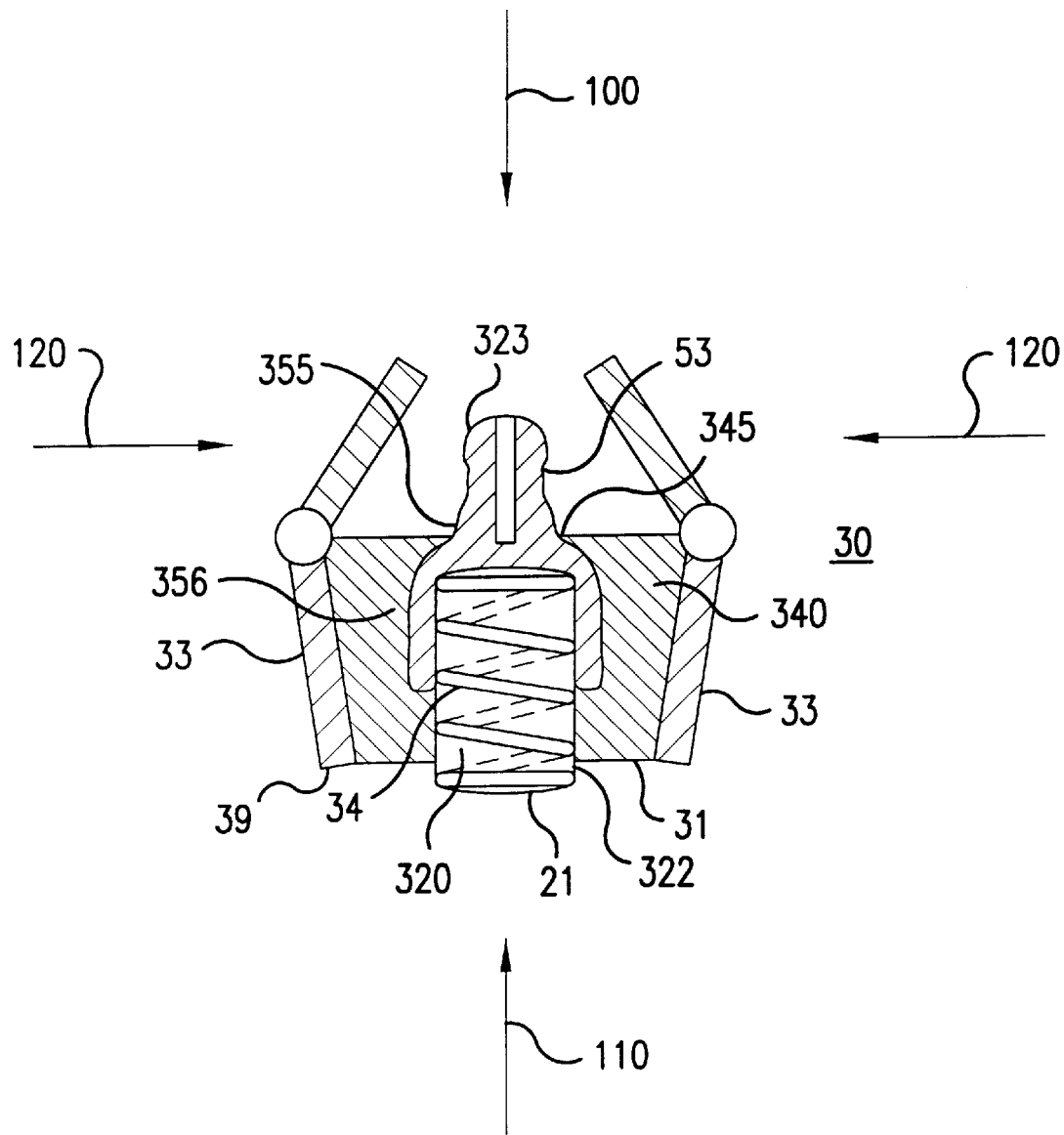
FIG. 3 is a cut-away view of a quick-placement EEG electrode.

In an alternative embodiment, as shown in FIG. 3, an the EEG electrode 30 includes a first element, and one or more second elements that connect to the first element and that operate in conjunction with the first element. In FIG. 3, the first element is shown as a cap 31, and the second elements are shown as pinning levers 33 and a plunger 53. The cap 31 includes a hollow, cylindrical upper portion 340 encapsulating a coil spring 34 protruding through the cap 31. Other configurations for the cap 31 are possible. For example, the cap 31 could be any polygon. The plunger 53 penetrates the cap 340 through an opening 345. In FIG. 3, the opening 345 is circular. However, the opening 345 may be any suitable shape, including that of any polygon. Also, as shown in FIG. 3, the plunger 53 includes a receptacle 323 that is used to attach the EEG electrode 30 to a recording device (not shown). The plunger 53 includes an upper section 355 and a lower section 356. In FIG. 3, the upper section 355 and the lower section 356 are cylindrical. However, the upper section 355 and the lower section 356 can be in the shape of any polygon to match the corresponding shape of the opening 345. The upper section 355 projects through the opening 345. A diameter of the lower section 356 is larger than a diameter of the opening 345, thereby preventing the plunger 53 from exiting through the opening 345. A sponge 320, saturated with an electrolytic gel 21, and covered by a membrane 322, is encapsulated within the lower section 356 of the plunger 53. The sponge 320 may have a cross section that corresponds to that of the lower section 356. For example, the sponge 320 may be cylindrical or in the shape of any polygon. Using the sponge 320 saturated with the gel 21 ensures that the gel 21 will not evaporate during the time that the EEG electrode 30 is attached to the patient's scalp.

The sponge 320 may be attached to the EEG electrode 30 immediately prior to use, or may be attached when the EEG electrode is manufactured, for example, as previously described in conjunction with FIG. 2.

The EEG electrode 30 is connected to an EEG lead wire (not shown) at receptacle 323. Various known connection devices may be used for this purpose, such as a collar connector, for example, as previously described in conjunction with FIG. 2.

The EEG electrode shown in FIG. 3 may be of a small size with a diameter of the cap being about 2 cm, for example. The cap 31 may be injection molded using acrylonitrile-butadiene-styrene (ABS) or similar material. The pinning levers 33 may be injected molded using Elastollan® thermoplastic polyurethane (TPU) or similar material or comprised of spring steel. The plunger 13 may be injection molded and may be made of a material similar to that of the pinning levers 33, and coated with a conducting material, for example, as previously described in conjunction with FIG. 2.

Figure 4:
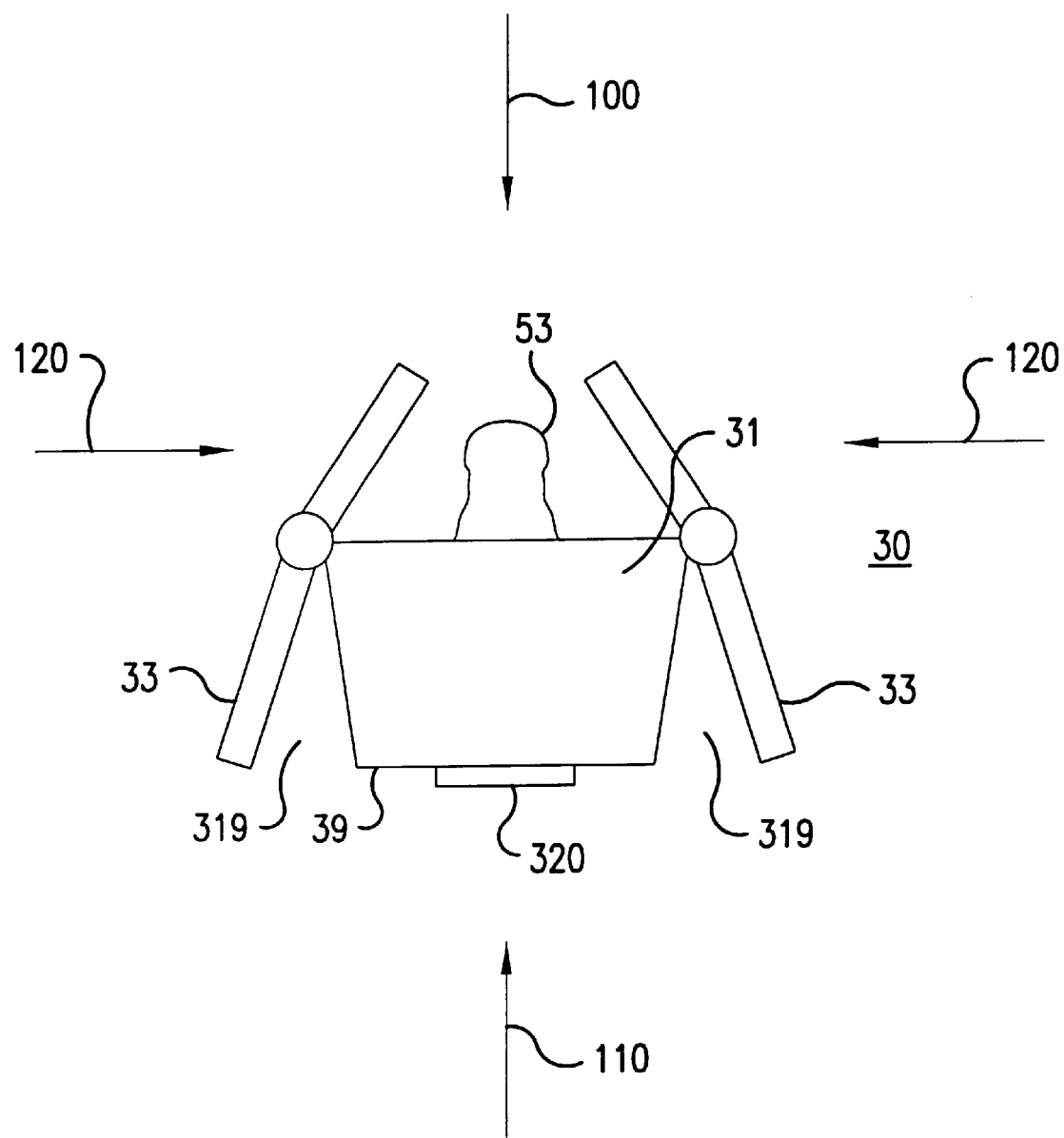
FIG. 4 is a side view of the quick placement EEG electrode of FIG. 3.

Once the EEG lead is connected, referring to FIG. 4, the pinning levers 33 are squeezed in the direction of arrows 120, which creates openings 319 between the pinning levers 33 and the bottom of the cap 39. The EEG electrode 30 is placed against the hair on the patient's scalp where recording is desired, with bottom portions 39 contacting the scalp, and the EEG electrode 30 pressed against the scalp in the general direction of the arrow 100, which causes the coil spring 34 (see FIG. 3) to compress. Some scalp hairs penetrate the openings 319 formed between the "open" pinning levers 33 and the cap 31. The pinning levers 33 are then released to trap the scalp hairs and hold the EEG electrode 30 in place.

The plunger 53 is then depressed with a downward force shown generally by the arrow 100, causing rapid compression of the sponge 320 in the center of the plunger 53. The compression of the sponge 320 ruptures the thin plastic membrane 322, causing the electrolytic gel 21 to be applied to the scalp contact point as previously described in conjunction with FIG. 2.

In addition to supplying the electrolytic gel 21, the compressed sponge 320 provides an additional upward force, shown generally by arrow 110, opposing a downward force being exerted by the hair trapped between the pinning levers 33 and the cap 31, thereby creating an equilibrium system. The sponge 320, acting as a shock absorber, maintains constant contact with the scalp, even if the EEG electrode 30 moves up or down in relation to the scalp. The EEG electrode 30 is easily removed by again compressing the pinning levers 33, and releasing the trapped hairs.

Figure 5:
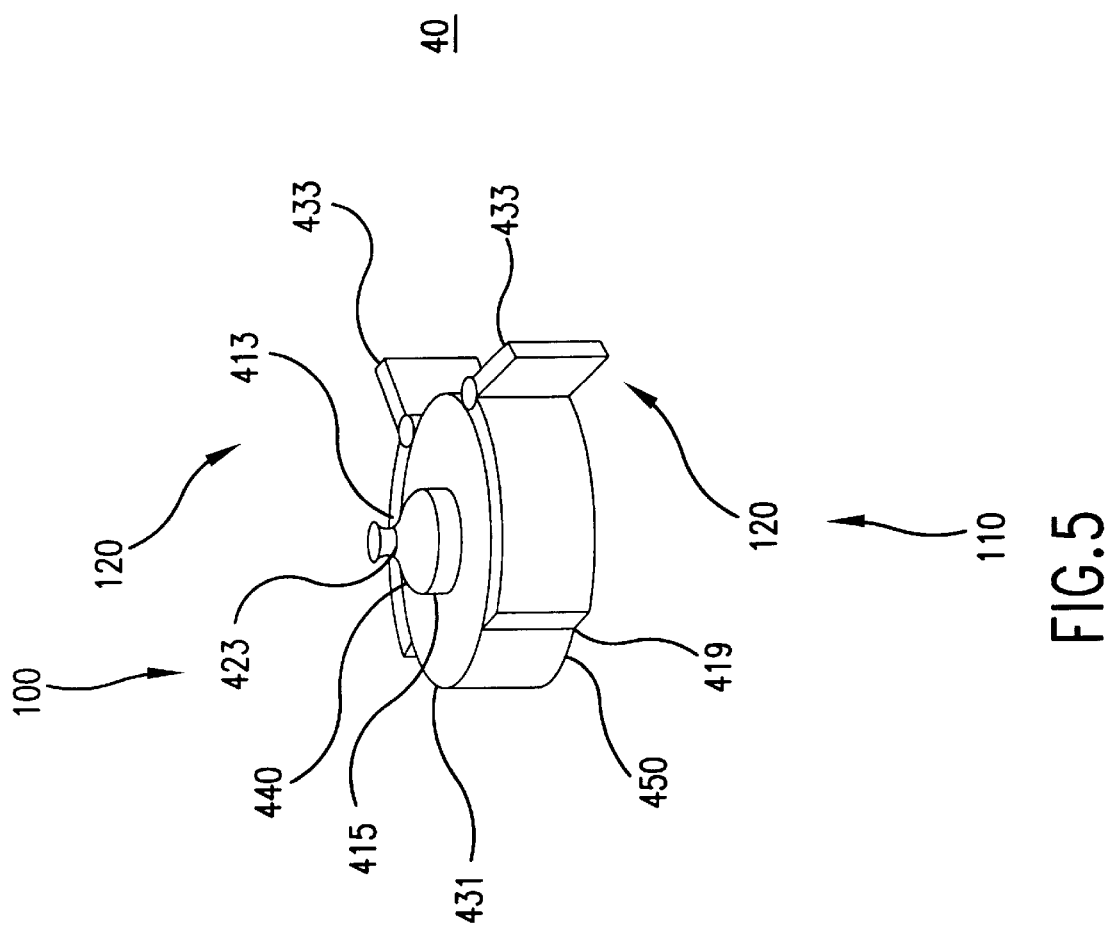
FIG. 5 is a perspective view of a quick-placement EEG electrode.

In another embodiment, as shown in FIG. 5, an EEG electrode 40 includes a first element, and one or more second elements that connect to the first element and that operate in conjunction with the first element. In FIG. 5, the first element is shown as a cap 431, and the second elements are shown as pinning levers 433 and a plunger 413. The cap 431 includes a hollow, cylindrical upper portion 440 encapsulating a coil spring (not shown) protruding through an opening (not shown) in a bottom 450 of the cap 431. Other configurations for the cap 431 are possible. For example, the cap 431 could be any polygon. The plunger 413 penetrates an upper portion of the cap 440 through an opening 415. In FIG. 5, the opening 415 is circular, however the opening 415 may be any suitable shape, including that of any polygon. Also, as shown in FIG. 5, the plunger 413 includes a receptacle 423 that is used to attach the EEG electrode 40 to a recording device (not shown). The plunger 413 includes an upper section (not shown) and a lower section (not shown). The upper section and the lower section are cylindrical. However the upper section and the lower section can be in the shape of any polygon to match the corresponding shape of the opening 415. The upper section projects through the opening 415. A diameter of the lower section is larger than a diameter of the opening 415, thereby preventing the plunger 413 from exiting through the circular opening 415. A sponge (not shown), saturated with an electrolytic gel (not shown), and covered by a membrane (not shown), is encapsulated within the lower section of the plunger 413 as previously described in conjunction with FIG. 2. The sponge may be attached to the EEG electrode 40 immediately prior to use, or may be attached when the EEG electrode is manufactured, for example, as previously described in conjunction with FIG. 2.

The EEG electrode 40 is connected to an EEG lead wire (not shown) at receptacle 423. Various known connection devices may be used for this purpose as previously described in conjunction with FIG. 2.

The EEG electrode 40 shown in FIG. 5 may be of a small size with a diameter of the cap being about 2 cm, for example. The cap 431 may be injection molded using acrylonitrile-butadiene-styrene (ABS) or similar material. The pinning levers 433 may be injected molded using Elastollan® thermoplastic polyurethane (TPU) or similar material or may be made of spring steel. The plunger 413 may be injection molded and may be made of a material similar to that of the pinning levers 433. The plunger 413 may be coated with a conducting material, for example, as previously described in conjunction with FIG. 2.

Once the EEG lead is connected, the pinning levers 433 are squeezed in the direction of arrows 120, which creates an opening 419 between the pinning levers 433 and the bottom of the cap 450. The EEG electrode 40 is placed against the hair on the patient's scalp where recording is desired, with the bottom portions 450 contacting the scalp. The EEG electrode 40 pressed against the scalp in the general direction of the arrow 100, which causes the coil spring 434 to compress. Some scalp hairs penetrate the opening 419 formed between the open pinning levers 433 and the cap 431. The pinning levers 433 are then released to trap the scalp hairs and hold the EEG electrode 40 in place.

The plunger 413 is then depressed with a downward force shown generally 100, causing rapid compression of the sponge in the center of the plunger 413. The operation of the sponge is as previously described in conjunction with FIG. 2.

The compressed sponge provides an additional upward force, shown generally by arrow 110, opposing a downward force being exerted by the hair trapped between the pinning levers 433 and the cap 431, thereby creating an equilibrium system. The sponge, acting as a shock absorber, maintains constant contact with the scalp, even if the EEG electrode 40 moves minutely up or down in relation to the scalp. The BEG electrode 40 is easily removed by again compressing the pinning levers 433, and releasing the trapped hairs.

Figure 6:
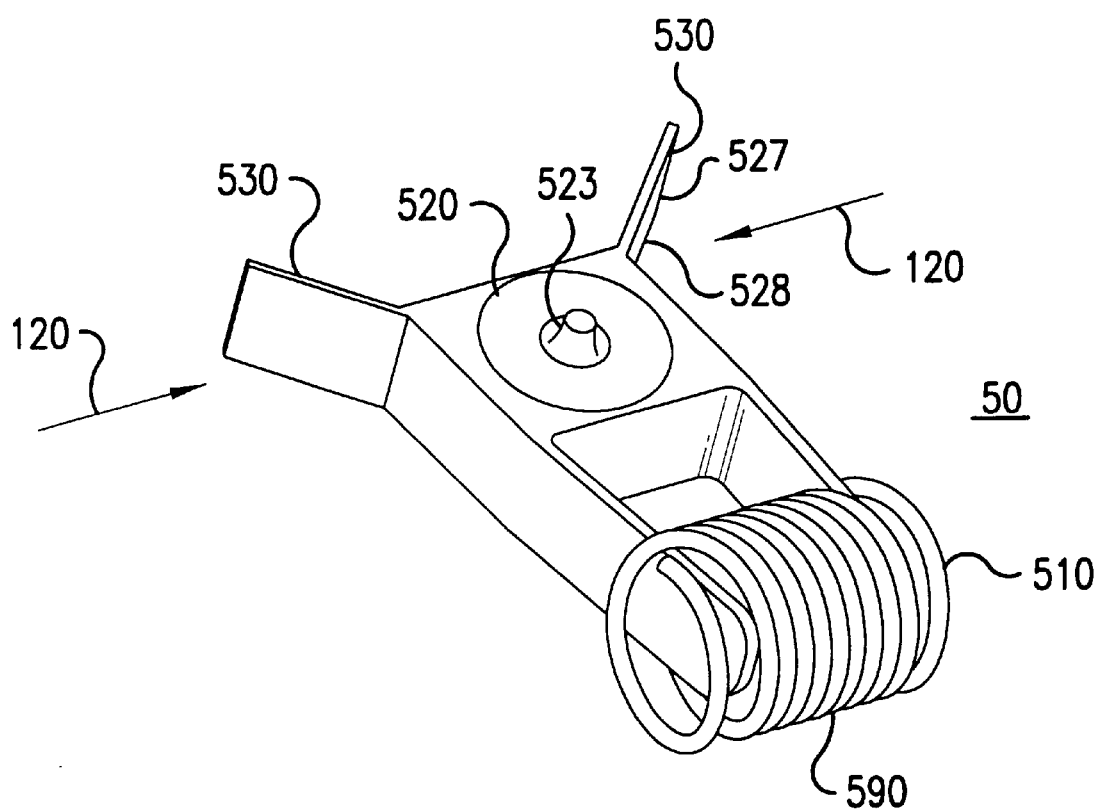
FIG. 6 is a perspective view of a quick-placement EEG electrode.

In an alternative embodiment, as shown in FIG. 6, an EEG electrode 50 includes a first element or fixed section, and a second element or movable section that connects to the first element and that operates in conjunction with the first element. In FIG. 6, the first element is shown as a coil spring 510, and the second element is shown as a pair of spring loaded pinning levers 530 mounted astride a central body 520. Also, as shown in FIG. 6, the pinning levers 530 include a receptacle 523 on the spring loaded hinge assembly 52 that is used to attach the EEG electrode 50 to a recording device (not shown). The pinning levers 530 are affixed to the coil spring 510. In FIG. 6, the coil spring 510 is shown as cylindrical, but could be square in cross section, for example.

The EEG electrode 50 is connected to an EEG lead wire (not shown) at receptacle 523. Various known connection devices may be used for this purpose, such as a collar connector, for example, as previously described in conjunction with FIG. 2.

The EEG electrode shown in FIG. 6 may be of a small size with an area of the EEG electrode 50 being about 2 cm square, for example. The pinning levers 530 and spring loaded hinge assembly 520 may be made using acrylonitrile-butadiene-styrene (ABS) or similar material or spring steel or other suitable metal. The pinning levers 530 and spring loaded hinge assembly 520 are coated with a conducting material, for example, as previously described in conjunction with FIG. 2.

Once the EEG lead is connected, the pinning levers 530 are squeezed in the direction of arrows 120 which opens the winds of the coil spring 510. The EEG electrode 50 is placed against the hair on the patient's scalp where recording is desired, with the bottom portions 590 of the coil spring 510 contacting the scalp. Some scalp hairs penetrate the openings formed between the open winds of the coil spring 510. The pinning levers 510 are then released to trap the scalp hairs in the closed winds of the coil spring 510 and hold the EEG electrode 50 in place. A sponge (not shown) saturated with electrolytic gel may be housed within the EEG electrodes 50 to complete the EEG circuit. The EEG electrode 50 is removed by again compressing the pinning levers 530 in the general direction of 120, and removing the EEG electrode 50 from the patient's scalp.

Figure 7:
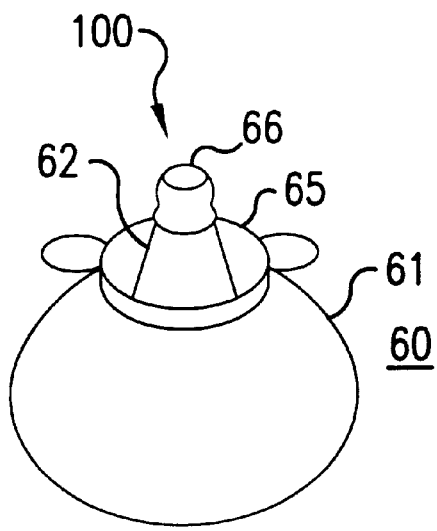
FIG. 7 is a perspective view of a quick-placement EEG electrode.

In yet another embodiment shown in FIG. 7, an EEG electrode 60 includes a first element or fixed section, and a second element or movable section that connects to the first element and that operates in conjunction with the first element. In FIG. 7, the first element is shown as a cap 61, and the second element is shown as hollow, conical shaped grabbing element 62. Other configurations for the cap 61 are possible. For example, the cap 61 could be any polygon. The grabbing element 62 penetrates the cap 61 through a circular opening 65.

Figure 8:
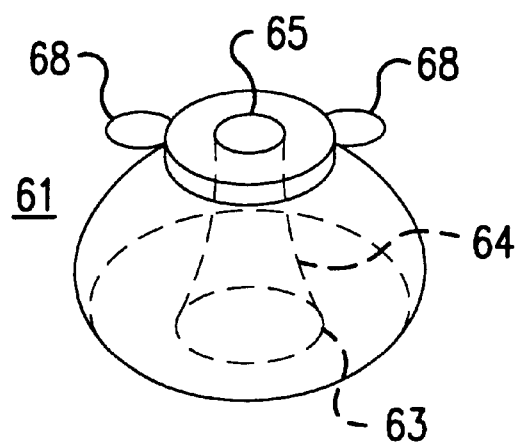
FIG. 8 is a perspective view of the cap of the quick-placement EEG electrode of FIG. 7.

Referring to FIG. 8, the EEG electrode 60 is shown with a hollow, conical interior 64 in phantom. The conical interior 64 generally corresponds to the shape of the grabbing element 62. The cap 61 includes an upper opening 65 and a lower opening 63. As shown in FIG. 8, the openings 65, 63 are circular, but could be any suitable shape. A diameter of the upper opening 65 is smaller than a diameter of the lower opening 63, thereby preventing the grabbing element 62 from exiting there through. The cap 61 also includes two lifting tabs 68.

Figure 9:
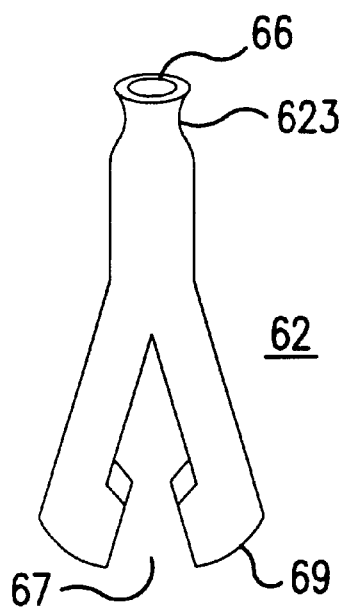
FIG. 9 is a perspective view of the grabbing element of the quick-placement EEG electrode of FIG. 7.
Figure 11A:
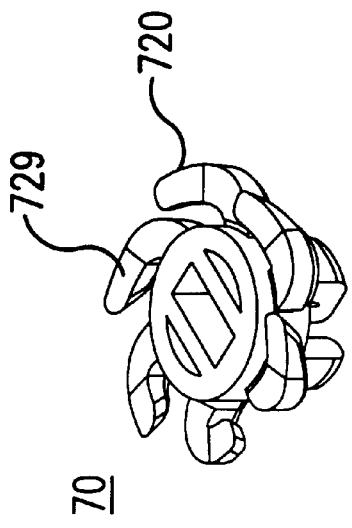
FIGS. 11a–11d are perspective views of components the quick-placement EEG electrode of FIGS. 10a–10d.
Figure 11B:
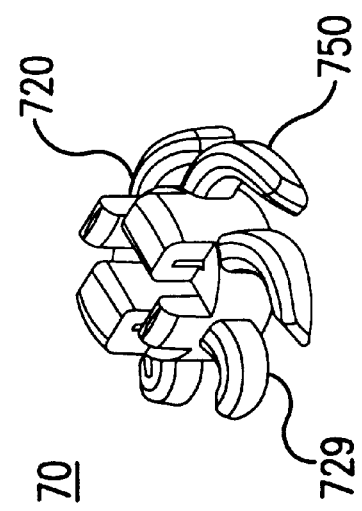
Figure 11C:
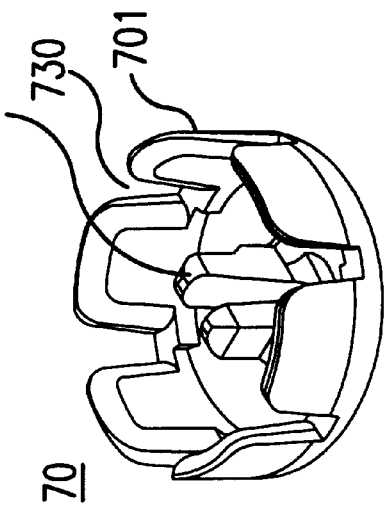
Figure 11D:
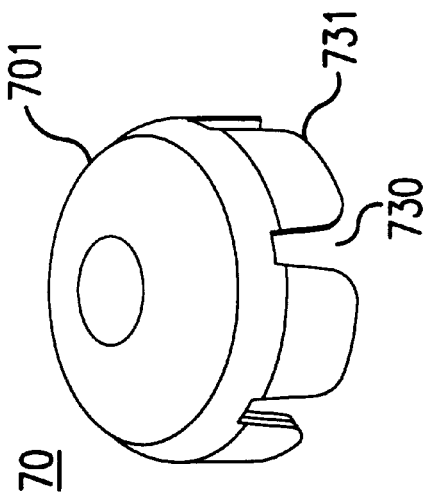

Referring to FIG. 9, the grabbing element 62 has an opening 67 that bisects the grabbing element 62, a circular opening 66 at a top, and a receptacle 623 for accepting a collar connector (not shown). As shown in FIG. 9, the grabbing element 62 is circular, however the grabbing element 62 could be any suitable shape, including any polygon.

The EEG electrode 60 is connected to an EEG lead wire (not shown) at a receptacle 623. Various known connection devices may be used for this purpose, such as a collar connector, for example, as previously described in conjunction with FIG. 2.

The EEG electrode shown in FIGS. 7–9 may be of a small size with a diameter of the cap 61 being about 2 cm, for example. The cap 61 may be injection molded using acrylonitrile-butadiene-styrene (ABS) or similar material. The grabbing element 62 may be injection molded using Elastollan® thermoplastic polyurethane (TPU) or similar material or comprised of spring steel. The grabbing element 62 is coated with a conducting material, for example, as previously described in conjunction with FIG. 2.

In use, the grabbing element 62 is placed against the hair on the patient's scalp where recording is desired, with the bottom portion 69 contacting the scalp. Some scalp hairs penetrate the opening 67. The cap 61 is then placed over the grabbing element 62, and pressed downward against the scalp in the general direction of 100, which causes the opening 67 to close and trap hairs in the now closed opening 67. The grabbing element 62 and the cap 61 frictionally fit together to hold the EEG electrode 60 in place. Electrolytic gel 21 may then be applied and replenished through the opening 66, after which the EEG lead is connected at the receptacle 623. The EEG electrode 60 is removed by disconnecting the EEG lead, and pressing down on the grabbing element 62 while simultaneously lifting the cap 61 upwards by the lifting tabs 68.

In another embodiment, FIGS. 10a–10d show a quick-placement EEG electrode 70 for use in recording brain wave activity, for example. The BEG electrode 70 includes a first element and one second element that connects to the first element and that operates in conjunction with the first element. In particular, the second element is movable with respect to the first element. In FIG. 10, the first element is shown as a cap 701 and the second element is a hair grabbing element 720. The hair grabbing element 720 is frictionally attached to an interior of the cap 701. The cap 701 includes a plurality of serrations 730 around its lower rim 731. Other configurations for the cap 701 are also possible, and the cap 701 could be in the shape of any polygon for example. The hair grabbing 720 element is attached to the cap 701 by the locking arms 740 located within the interior of the cap 701.

Referring to FIGS. 11a–11d, the hair grabbing element 720 is circular in shape with a series of scimitar like protrusions 750 thereabout corresponding to the serrations 730 in the cap 701. The EEG electrode 70 may be of small size, with the area of the cap 701 being about 2 cm square for example. The cap 701 may be injection molded using acrylonitrile-butadiene-styrene (ABS) or similar material. The hair grabbing element 720 may be injection molded using Elastollan® thermoplastic polyurethane (TPU) or similar material, or comprised of an electrically conductive plastic. Alternatively, the hair grabbing element may be coated with a conducting material as previously described in conjunction with FIG. 2.

Once a EEG lead wire is connected to the EEG electrode 70, the EEG electrode 70 is placed against the hair at a point on the patient's scalp where recording is desired, with the bottom portion 729 of the hair grabbing element 720 contacting the scalp. The cap 701 is then rotated clockwise, which causes the protrusions 750 to rake along the scalp and lift scalp hairs onto the protrusions 750. The cap 701 is then depressed, which causes the scalp hairs to become trapped between the protrusions 750 and the corresponding serrations 730 in the cap 701. The EEG electrode 70 is removed by pressing the hair grabbing device 720 downward through the opening 760 in the center of the cap 701.

Figure 12B:
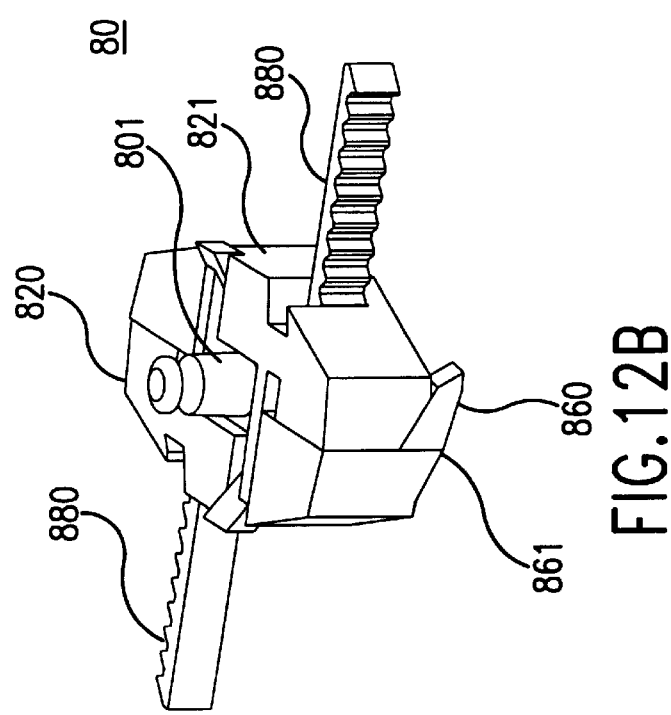
FIGS. 12a–12b are perspective views of a quick-placement EEG electrode.
Figure 12A:
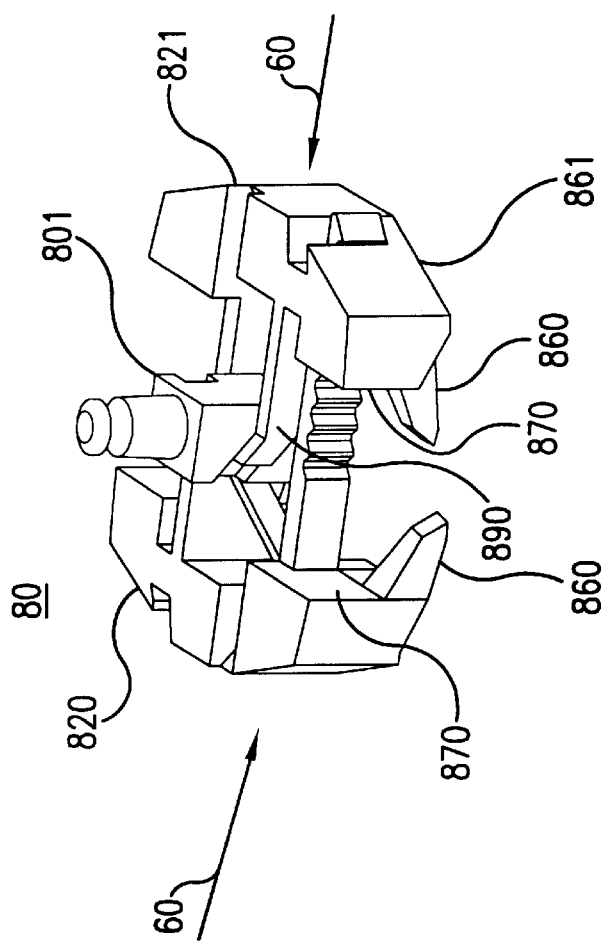

Another embodiment, shown in FIGS. 12a and 12b, is in a quick-placement EEG electrode 80 for use in recording brain wave activity, for example. The EEG electrode 80 includes a first element and two second elements that connect to the first element and that operate in conjunction with the first element. In particular, the second elements are movable relative to the first element. In FIG. 12b, the first element is shown as a body 801. The second element may include two symmetrical hair grabbing elements 820, 821. The hair grabbing elements 820, 821 are fitted to the body 801 using a symmetrical ratcheting mechanism 880. The grabbing elements 820, 821 also have two tabs, 860, 890. The lower tab 860 serves to rake along the scalp and raise hairs while the upper tab 890 functions to guide the grabbing element 820, 821 along the body 801.

The EEG electrode 80 may be of small size, with the area of the body 801 being about 2 cm square for example. The body 801 may be injection molded using acrylonitrile-butadiene-styrene (ABS) or similar material. The hair grabbing elements 820, 821 may be injection molded using Elastollan® thermoplastic polyurethane (TPU) or similar material, or comprised of an electrically conductive plastic. Alternatively, the hair grabbing elements 820, 821 may be coated with a conducting material as previously described in conjunction with FIG. 2.

Once a EEG lead wire is connected to the EEG electrode 80, the EEG electrode 80 is placed against the hair at a point on the patient's scalp where recording is desired, with the bottom portions 861 of the hair grabbing elements 820, 821 contacting the scalp. The hair grabbing elements are then pressed together in the general direction of arrow 60. This causes the lower tabs 860, to rake along the scalp and lift hairs. Once the hair grabbing elements 820, 821 are fully pressed against the body 801, the raised scalp hairs are captured between the opposing faces 870 of the hair grabbing elements 820, 821. The EEG electrode 80 is held in the closed position by operation of the ratcheting mechanism 880.

Figure 13A:
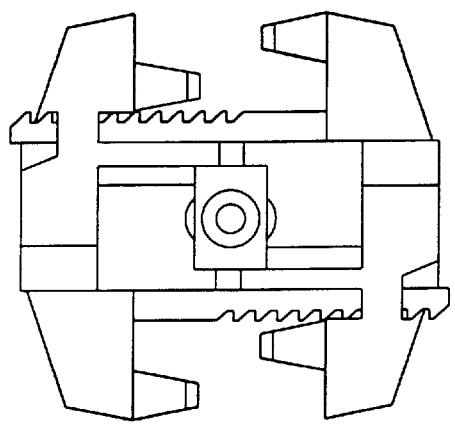
FIGS. 13a–13b are top views of the quick-placement EEG electrode of FIGS. 12a–12b.
Figure 13B:
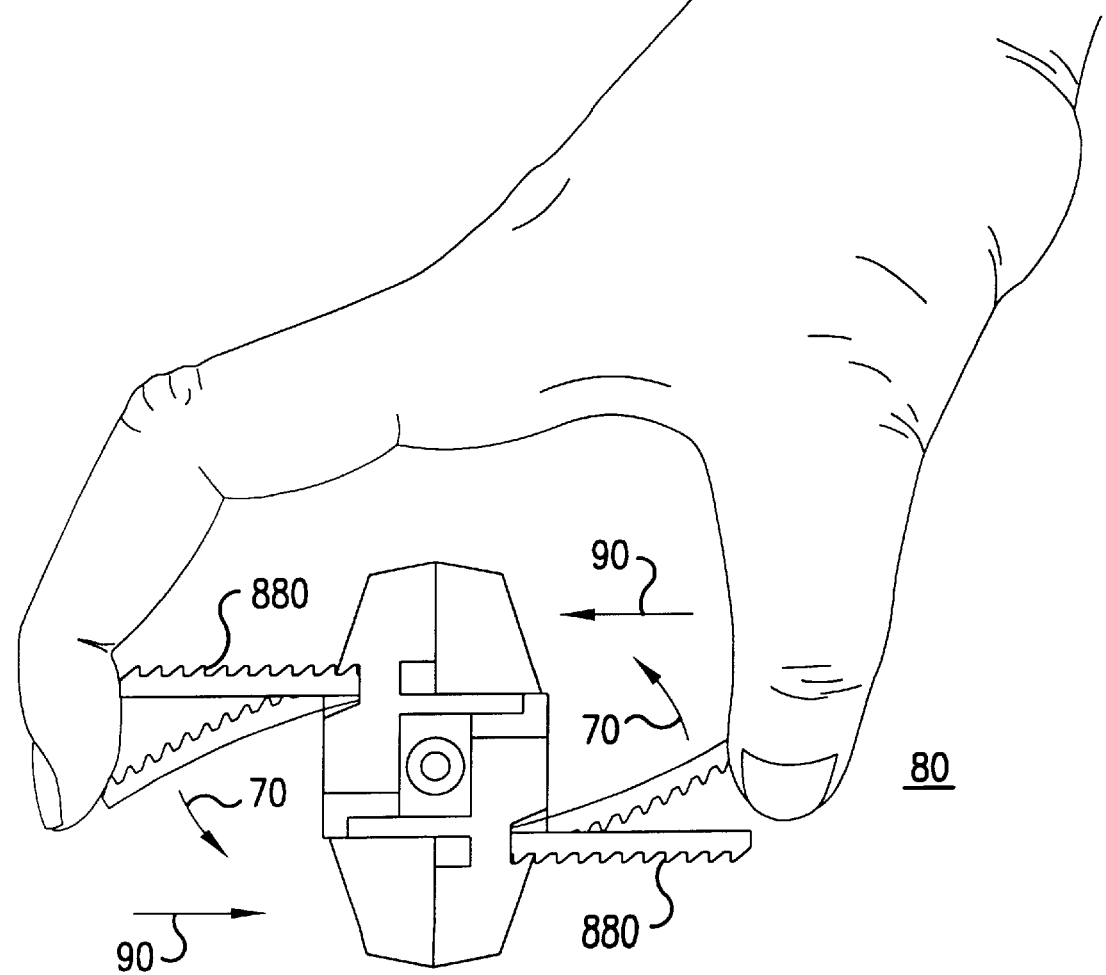

Referring to FIGS. 13a–b, the EEG electrode 80 is easily removed by deflecting the ratcheting mechanism 880 in the general direction of arrows 70, and simultaneously pressing inward on the ratcheting mechanism 880 in the general direction of arrows 90.

While the invention has been described in conjunction with the specific embodiments outlined above, it is evident that many alternatives, modifications and variations will be apparent to those skilled in the art. Accordingly, the preferred embodiments of the invention are intended to be illustrative and not limiting. Various changes may be made without departing from the spirit and scope of the invention as defined in the following claims.

What is claimed is:

1. A quick placement electrode for attachment to a patient's scalp, comprising:

a cap having a central cavity; and a grabbing element, the grabbing element extending through the central cavity and capable of vertical movement within the central cavity between an engaged position and a disengaged position, wherein downward pressure of the cap onto the grabbing element causes the grabbing element to bind hairs within the grabbing element, the electrode being held in place by a force one the bound hairs created by the grabbing element.

2. The quick placement electrode of claim 1, wherein the cap is injection-molded and made from a flexible material including acrylonitrile-butadiene-styrene.

3. The quick placement electrode of claim 1, wherein the grabbing element is injection-molded and made from a flexible material including polyurethane.

* * * * *

UNITED STATES PATENT AND TRADEMARK OFFICE
CERTIFICATE OF CORRECTION

PATENT NO. : 6,175,753 B1
DATED : January 16, 2001
INVENTOR(S) : Alex Menkes et al.

It is certified that error appears in the above-identified patent and that said Letters Patent is hereby corrected as shown below:

Column 2,
Line 28, delete "patient'share" and substitute -- patient's hair --;

Column 3,
Line 63, delete "patient'sscalp" and substitute -- patient's scalp --;

Column 12,
Line 4, delete "one" and substitute -- on --.

Signed and Sealed this

Twenty-fifth Day of December, 2001

JAMES E. ROGAN
Director of the United States Patent and Trademark Office